US009345882B2

(12) United States Patent
Moulder et al.

(10) Patent No.: US 9,345,882 B2
(45) Date of Patent: May 24, 2016

(54) IMPLANTABLE MEDICAL DEVICE VOLTAGE DIVIDER CIRCUIT FOR MITIGATING ELECTROMAGNETIC INTERFERENCE

(71) Applicant: PACESETTER, INC., Sylmar, CA (US)

(72) Inventors: J. Christopher Moulder, Portland, OR (US); Peter Boileau, Valencia, CA (US)

(73) Assignee: PACESETTER, INC., Sylmar, CA (US)

( * ) Notice: Subject to any disclaimer, the term of this patent is extended or adjusted under 35 U.S.C. 154(b) by 241 days.

(21) Appl. No.: 14/243,702

(22) Filed: Apr. 2, 2014

(65) Prior Publication Data

US 2014/0214108 A1    Jul. 31, 2014

Related U.S. Application Data

(62) Division of application No. 12/968,563, filed on Dec. 15, 2010, now Pat. No. 8,725,256.

(51) Int. Cl.
*A61N 1/37* (2006.01)
*A61N 1/36* (2006.01)
*A61N 1/362* (2006.01)

(52) U.S. Cl.
CPC ............ *A61N 1/36125* (2013.01); *A61N 1/362* (2013.01); *A61N 1/36142* (2013.01); *A61N 1/37* (2013.01); *A61N 1/3718* (2013.01)

(58) Field of Classification Search
CPC ....... A61N 1/362; A61N 1/37; A61N 1/3718; A61N 1/36125; A61N 1/36142
USPC ........................................... 607/9, 62, 63, 65
See application file for complete search history.

(56) References Cited

U.S. PATENT DOCUMENTS

| 6,209,764 B1 | 4/2001 | Harlaub et al. |
| 6,424,234 B1 | 7/2002 | Stevenson |
| 6,765,779 B2 | 7/2004 | Stevenson et al. |
| 6,901,292 B2 | 5/2005 | Hrdlicka et al. |
| 7,038,900 B2 | 5/2006 | Stevenson et al. |
| 7,162,302 B2 | 1/2007 | Wang et al. |

(Continued)

OTHER PUBLICATIONS

Restriction Requirement, mailed Jul. 16, 2013—U.S. Appl. No. 12/968,563.

(Continued)

*Primary Examiner* — Theodore Stigell
*Assistant Examiner* — Michael Carey

(57) ABSTRACT

An RF protection circuit mitigates potentially adverse effects that may otherwise result from electromagnetic interference (e.g., due to MRI scanning of a patient having an implanted medical device). The RF protection circuit may comprise a voltage divider that is deployed across a pair of cardiac electrodes that are coupled to internal circuitry of the implantable medical device. Each leg of the voltage divider may be referenced to a ground of the internal circuit, whereby the different legs are deployed in parallel across different circuits of the internal circuitry. In this way, when an EMI-induced (e.g., MRI-induced) signal appears across the cardiac electrodes, the voltages appearing across these circuits and the currents flowing through these circuits may be reduced. The RF protection circuit may be used in an implantable medical device that employs a relatively low capacitance feedthrough to reduce EMI-induced (e.g., MRI-induced) current flow in a cardiac lead.

6 Claims, 9 Drawing Sheets

(56) References Cited

U.S. PATENT DOCUMENTS

| | | |
|---|---|---|
| 7,164,950 B2 | 1/2007 | Kroll et al. |
| 7,181,276 B1 | 2/2007 | Province et al. |
| 7,941,226 B2 | 5/2011 | Marshall |
| 8,494,649 B2 | 7/2013 | Stancer et al. |
| 2003/0204217 A1 | 10/2003 | Greatbatch |
| 2005/0197677 A1 | 9/2005 | Stevenson |
| 2007/0083244 A1 | 4/2007 | Stevenson et al. |
| 2007/0112398 A1* | 5/2007 | Stevenson ............ A61N 1/05 607/63 |
| 2011/0112599 A1* | 5/2011 | Zhang ............ A61N 1/3718 607/37 |

OTHER PUBLICATIONS

NonFinal Office Action, mailed Sep. 9, 2013—U.S. Appl. No. 12/968,563.

Notice of Allowance, mailed Jan. 8, 2014—U.S. Appl. No. 12/968,563.

* cited by examiner

IMPLANTABLE MEDICAL DEVICE VOLTAGE DIVIDER CIRCUIT FOR MITIGATING ELECTROMAGNETIC INTERFERENCE

CROSS REFERENCE TO RELATED APPLICATIONS

This application is a division of U.S. patent application Ser. No. 12/968,563, filed Dec. 15, 2010, entitled "Implantable Medical Device Voltage Divider Circuit for Mitigating Electromagnetic Interference," which is incorporated herein by reference.

TECHNICAL FIELD

This application relates generally to implantable medical devices and more specifically, but not exclusively, to circuitry for mitigating effects of electromagnetic interference (e.g., that may result from MRI scanning of a patient with an implanted medical device).

BACKGROUND

An implantable medical device may connect to one or more implantable conductors that are outside of the device. For example, an implantable cardiac rhythm management device (e.g., a pacemaker, a defibrillator, or a cardioverter) may connect to one or more leads implanted in or near the heart of a patient to monitor cardiac function and provide therapy for a patient who suffers from cardiac arrhythmia. For example, the implantable device may process signals received via implanted cardiac leads to track the type and timing of native cardiac signals. In the event cardiac events are not occurring at appropriate times or undesired cardiac events are detected, the implantable device may apply cardiac stimulation signals (e.g., pacing signals) to the heart via the implanted cardiac leads in an attempt to restore normal cardiac rhythm.

Under certain circumstances, however, unintentional pacing may occur when a patient with an implantable medical device is subjected to strong electromagnetic fields. For example, time-varying magnetic fields generated during magnetic resonance imaging (MRI) may induce currents in an implanted lead that may, in turn, stimulate (e.g., cause capture of) cardiac tissue. In some cases, this unintended pacing may cause cardiac fibrillation. Such MRI-induced currents may arise in different ways.

In some cases, pulsed magnetic gradients used during MRI scanning may induce voltage in an implanted cardiac lead connected to an implanted device. If such voltage appears across sufficiently low impedance, the resulting current flowing through the lead may cause stimulation of the heart.

In some cases, pulses of amplitude modulated radiofrequency ("RF") energy from MRI scanning (e.g., with a carrier at 64 MHz or 128 MHz) may enter the implantable medical device, whereupon the pulses are rectified by internal circuitry of the implantable medical device. The rectified signal may then exit the implantable medical device as a lower frequency demodulated signal on the implanted lead. This lower frequency signal may then travel to the patient's heart via the implanted lead and potentially cause unintended stimulation.

In view of the above, a physician may elect to not prescribe MRI scanning for a patient who has an implanted medical device. Consequently, such a patient may receive suboptimal treatment. Accordingly, a need exists for implantable medical devices that are sufficiently immune to the influence of MRI magnetic fields and other electromagnetic interference (EMI). This would enable, for example, a patient who has an implanted MRI-compatible medical device to have no extra restrictions going under an MRI scan as compared to a patient who does not have such an implanted device.

SUMMARY

A summary of several sample aspects of the disclosure follows. It should be appreciated that this summary is provided for the convenience of the reader and does not wholly define the breadth of the disclosure. For convenience, one or more aspects of the disclosure may be referred to herein simply as "some aspects".

The disclosure relates in some aspects to a protection circuit for mitigating potential effects of EMI. For example, a protection circuit as taught herein may be used to mitigate potentially adverse effects that may otherwise be caused by signals that are generated as a result of MRI scanning of a patient with an implantable medical device. In some aspects, the protection circuit reduces MRI-induced voltage across internal circuitry of an implantable medical device during MRI scanning. By reducing MRI-induced voltage in this manner, the protection circuit prevents these signals from being rectified by the internal circuitry and then exiting the implantable medical device as lower frequency demodulated signals that are capable of stimulating the heart.

In some aspects, a protection circuit as taught herein comprises a capacitive voltage divider that is deployed across cardiac electrodes (e.g., at least one cardiac lead electrode and, optionally, a case electrode) that are coupled to the internal circuitry. Here, each leg of the voltage divider may be referenced to a ground of the internal circuitry, whereby the different legs are deployed in parallel across different circuits of the internal circuitry. In this way, when an EMI-induced signal (e.g., an MRI-induced RF signal) appears across the cardiac electrodes, the voltages appearing across these circuits and the currents flowing through these circuits may be reduced (e.g., by up to a factor of 2). By reducing the voltages and currents in this manner, any components of these circuits that have the capability of rectifying an EMI-induced signal appearing across the cardiac electrodes may be prevented from performing such rectification.

Advantageously, the capacitive voltage divider circuit operates only on RF signals without significantly affecting the cardiac signals that the internal circuitry is intended to sense and without significantly affecting cardiac stimulation (e.g., pacing) signals intentionally generated by the internal circuitry. This is because the capacitors provide a low impedance at the high frequencies associated with, for example, the MRI-induced signals and provide high impedance at the lower frequencies associated with cardiac pacing and/or cardiac sensing.

In some aspects, a capacitive voltage divider as taught herein may be used in conjunction with several input protection diodes to provide additional reduction of RF voltage across internal circuitry. Here, each leg of the capacitive voltage divider is placed in parallel with a fast-switching diode. The diode is arranged such that it does not become forward-biased during normal device operation. For example, in a negative-ground system in which all input/output terminals have a higher potential than ground, the anode of each diode is connected to ground. However, the capacitive voltage divider begins to operate in the presence of an RF signal, raising the internal device ground potential above that of each input/output terminal for alternating ½ cycles. If the voltage across either protection diode becomes large enough to forward-bias it, then the two diodes begin to conduct in a balanced fashion on alternate ½ cycles; effectively clipping the RF voltage across each leg of the capacitive voltage divider and therefore across internal circuitry to one forward-biased diode voltage drop.

In some aspects, the protection circuit may be used in conjunction with a feedthrough circuit in which capacitance has been reduced (e.g., to 1.5 nanofarads from 4.7 nanofarads) in order to mitigate the hazard of unwanted cardiac stimulation due to pulsed magnetic gradients during MRI. Here, the lower capacitance value reduces current flow due to induction by pulsed magnetic gradients in a cardiac lead coupled to the implantable medical device. By reducing this current flow, the likelihood that the current flow may cause unwanted cardiac stimulation is reduced. In practice, the use of a lower capacitance feedthrough circuit may result in an increase in the RF energy injected into the internal circuitry of the implantable medical device. However, by deploying a protection circuit across the internal circuitry as taught herein, this energy may be prevented from affecting the internal circuitry.

An improved EMI filter (e.g., MRI filter) is thus provided through the use of protection circuitry that is referenced to ground in accordance with the teachings herein. For example, effective MRI-related filtering may be achieved via a simpler design and with a lower component count than may be achieved, for example, by a filter that is deployed in series with the cardiac leads.

BRIEF DESCRIPTION OF THE DRAWINGS

These and other features, aspects, and advantages will be more fully understood when considered with respect to the following detailed description, the appended claims, and the accompanying drawings, wherein:

Figure 1:
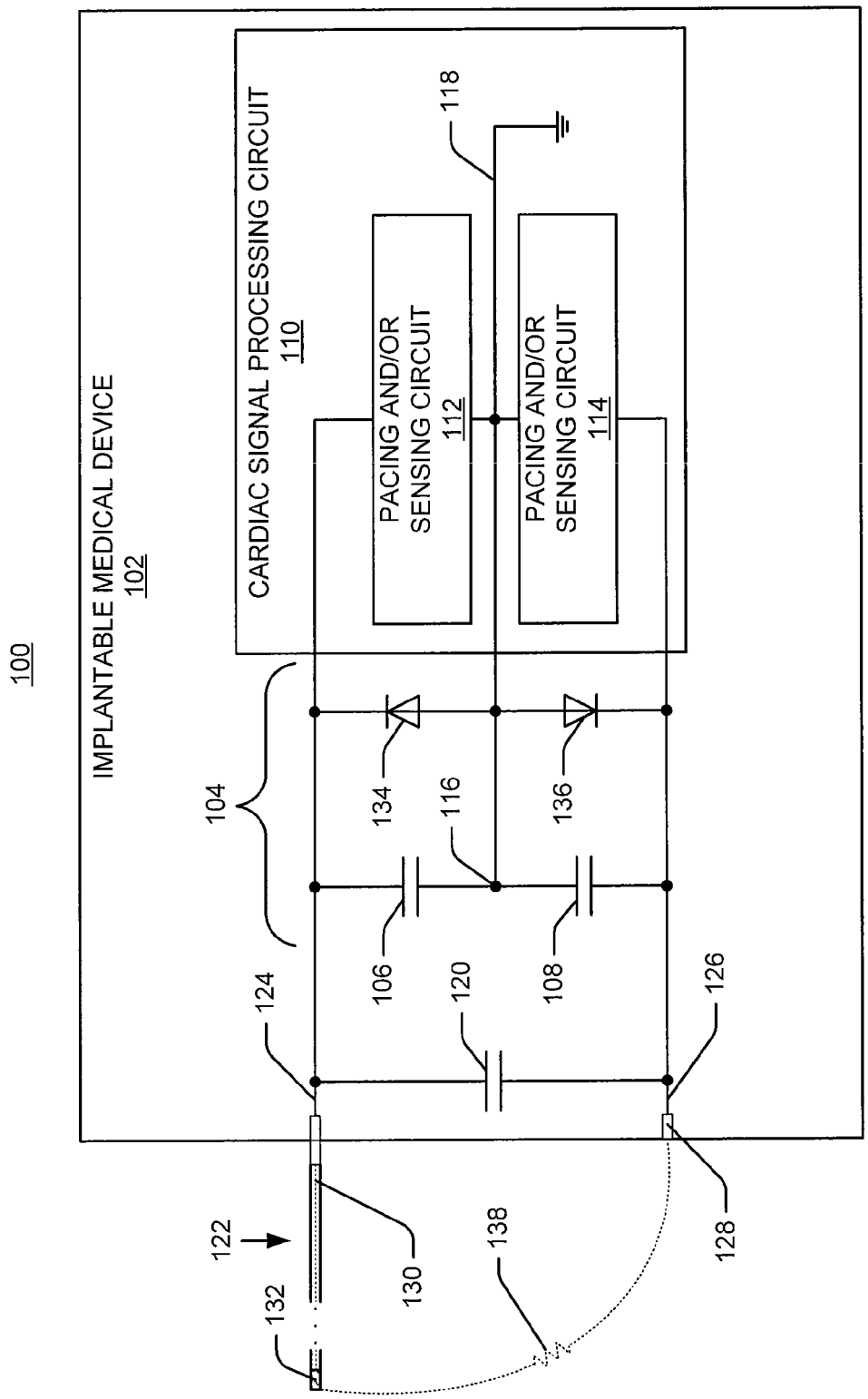
FIG. 1 is a simplified diagram of an embodiment of an implantable medical device comprising a circuit that filters MRI-induced signals.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

FIG. 1 illustrates an embodiment of an implantable medical apparatus 100 comprising an implantable medical device 102 configured for stimulating cardiac tissue and/or sensing cardiac activity. The device 102 includes a voltage divider circuit 104 comprising capacitors 106 and 108. The voltage divider circuit 104 acts to prevent MRI-induced signals that may enter the device 102 via an implantable cardiac lead 122 from being rectified by a cardiac signal processing circuit 110 (e.g., cardiac pacing circuitry and/or cardiac sensing circuitry) of the device 102. In this way, the voltage divider circuit 104 may reduce the likelihood that rectified signals will exit the device 102 via the cardiac lead 122 and stimulate cardiac tissue.

As discussed in more detail below, each leg (e.g., each capacitor 106 or 108) of the voltage divider circuit 104 is provided in parallel across corresponding circuitry (e.g., pacing and/or sensing circuit 112 or 114) of the cardiac signal processing circuit 110. Here, a center tap 116 of the voltage divider circuit 104 is coupled to a circuit ground 118 of the circuit 110. Accordingly, current that may otherwise flow into the circuits 112 and 114 may instead flow through the voltage divider circuit 104 to the circuit ground 118. Moreover, a lower overall load impedance (with respect to a "source" that generates the MRI-induced current) is provided by the placement of the voltage divider circuit 104 in parallel with the circuit 110. Consequently, a lower voltage is induced across the circuit 110, thereby reducing the likelihood that the circuit 110 will output a rectified signal.

In practice, an implantable medical device will typically use a feedthrough capacitor (e.g., capacitor 120) to provide a first layer of protection against electromagnetic interference (EMI). For example, the feedthrough capacitor may shunt high frequency current directly to the housing (e.g., case electrode 128) of the device 102 and away from internal circuitry of the device 102. Being physically located at the point where conductors enter the housing, the feedthrough capacitor may shunt current away from the conductors at a point before the conductors enter the housing, thereby reducing the likelihood that high frequency energy may re-radiate from the conductors within the housing.

In some implementations, a voltage divider circuit is employed in an implantable medical device that uses a feedthrough capacitor that has relatively low capacitance value (e.g., less than 2 nanofarads). Here, the duration of the MRI-induced current, and therefore also the amount of charge which may flow due to induction from pulsed magnetic fields in an implantable medical device, may be reduced by using smaller feedthrough capacitors (i.e., by using a capacitor with a smaller nominal capacitance value). For example, if the only path for charge (Q) is through the feedthrough capacitor, the reduction in charge is proportional to the reduction in capacitance (C) for a voltage step of magnitude V according to the relationship Q=CV.

The use of a lower capacitance value for the feedthrough capacitor results in a decrease of the net charge which can flow due to a change in voltage in a current loop path including, in the example of FIG. 1, a conductor 130 of the cardiac lead 122, circuitry of the device 102 coupled between terminals 124 and 126, and a return path through the case electrode 128 of the device and through patient tissue back to the cardiac lead. In FIG. 1, the current path through the patient tissue is represented in a simplified manner by a dashed line 138. Consequently, current flow (e.g., due to pulsed gradient-induced voltage) through this path is reduced, thereby reducing the likelihood that this MRI-induced current flow will stimulate cardiac tissue.

The use of a higher impedance feedthrough capacitor 120 would normally cause a higher RF voltage to appear across the circuit 110. However, as discussed above, the voltage divider circuit 104 reduces the amount of MRI-induced RF voltage that appears across either circuit 112 or 114. Thus, the voltage divider circuit 104 compensates for adverse effects that may otherwise result from the use of a smaller feedthrough capacitor.

Moreover, the voltage divider circuit 104 may prevent MRI-induced cardiac stimulation without significantly affecting other operations of the device 102. For example, while the capacitors 106 and 108 provide a low impedance (e.g., 1-4 ohms) at frequencies (e.g., approximately 64 MHz or 128 MHz) associated with MRI scanning, the capacitors 106 and 108 provide a higher impedance (e.g., >1 Mohm) at frequencies associated with cardiac pacing and cardiac sensing (e.g., on the order of kilohertz or less). Consequently, pacing pulses output by the device 102 or cardiac signals to be sensed by the device 102 are not affected by the voltage divider circuit 104.

FIG. 1 also illustrates that in some implementations the implantable medical device 102 may include input protection diodes 134 and 136 (e.g., fast-switching diodes). In accordance with the teachings herein, a capacitive voltage divider may be used in conjunction with the diodes 134 and 136 to provide additional reduction of RF voltage across the circuit 110. Here, the capacitor 106 is in parallel with the diode 134 and the capacitor 108 is in parallel with the diode 136. The diodes 134 and 136 are arranged so that they are not forward-biased during normal device operation. For example, in a negative-ground system where input/output terminals (corresponding to the electrode circuits 124 and 128) of the device 102 have a higher potential than the ground circuit 118, the anodes of the diodes 134 and 136 are coupled to the ground circuit 118 as shown in FIG. 1. In the presence of an RF signal, however, the capacitive voltage divider (capacitors 106 and 108) begins to operate, thereby raising the internal device ground potential (ground circuit 118) above that of each input/output terminal for alternating ½ cycles. If the voltage across either diode 134 or 136 becomes large enough to forward-bias the diode, the two diodes 134 and 136 begin to conduct in a balanced fashion on alternate ½ cycles; effectively clipping the RF voltage across each leg of the capacitive voltage divider (and therefore across each circuit 112 and 114) to one forward-biased diode voltage drop.

A capacitive voltage divider as taught herein may be implemented with various types of electrode circuits. In the example of FIG. 1, the electrode circuit 124 is electrically coupled to an electrode 132 (e.g., a tip or ring circuit) of the cardiac lead 122 while the electrode circuit 126 is electrically coupled to the case electrode 128. Other implementations, however, may employ multiple cardiac leads or cardiac leads with multiple electrodes. For example, the electrode circuit 126 may be electrically coupled to an electrode in another implantable cardiac lead (not shown). Alternatively, the electrode circuits 124 and 126 may be electrically coupled to electrodes (e.g., bi-polar tip and ring electrodes) of a single cardiac lead.

With the above overview in mind, additional details regarding how a capacitive voltage divider as taught herein may be employed to prevent MRI-induced cardiac stimulation will be described with reference to FIGS. 2-4. For purposes of illustration these figures describe an external interface (e.g., an input/output stage) of a cardiac stimulation device that includes a sample implementation of a pacing output stage. To reduce the complexity of these figures, other circuitry (e.g., sensing circuitry and/or other pacing circuitry) that may be employed in conjunction with the external interface is not shown. In addition, it should be appreciated that the teachings herein are applicable to other types of circuits.

Figure 2:
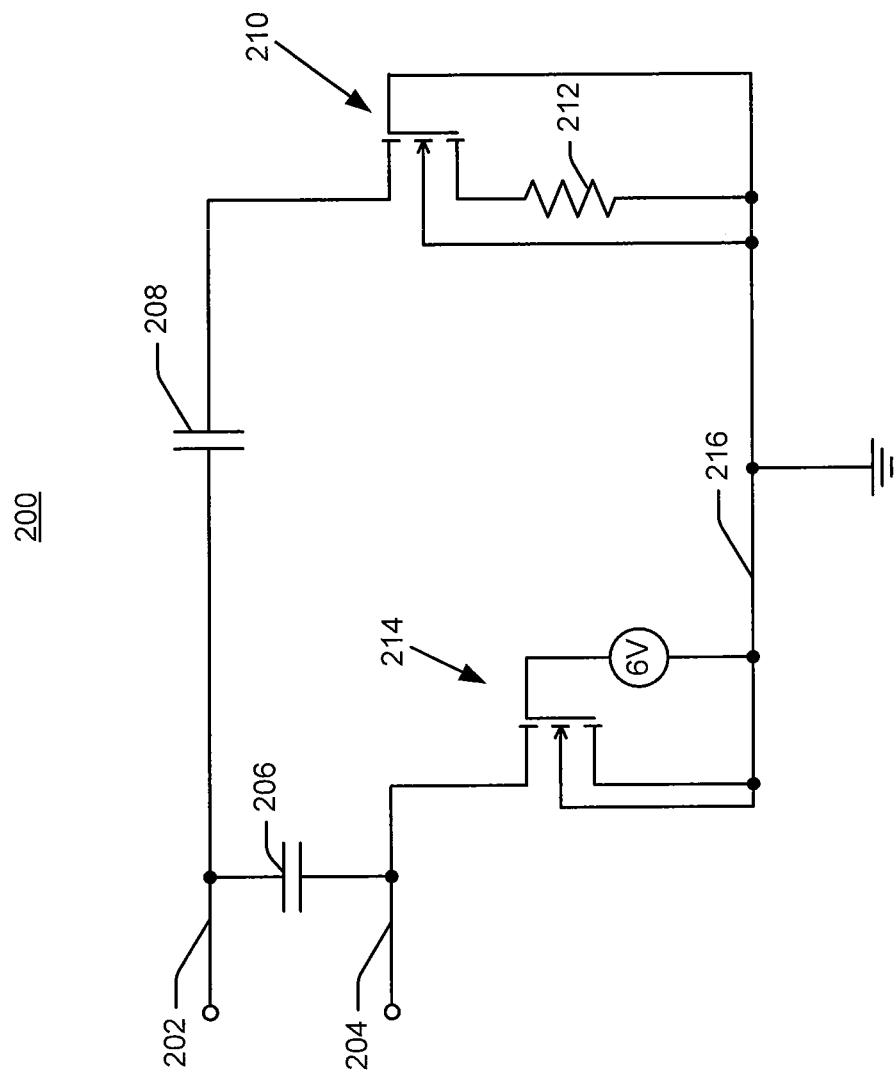
FIG. 2 is a simplified diagram illustrating sample internal circuitry for an implantable medical device.

FIG. 2 depicts a cardiac stimulation device 200 including a sample implementation of a pacing output stage. Electrode circuits 202 and 204 are configured to couple the pacing output stage to external electrodes (e.g., a cardiac lead electrode or a case electrode, not shown in FIG. 2). A feedthrough capacitor 206 is employed across the electrode circuits 202 and 204 as described herein. The pacing output stage includes a pacing series capacitor 208 (e.g., 4.7 microfarads or some other suitable value), a return switch 210 and associated return resistor 212 (e.g., 7.5 ohms or some other suitable value), and a fast discharge switch 214. The pacing output stage circuits here are referenced to a circuit ground 216 (e.g., device ground). The inputs of the device 200 (i.e., the electrode circuits 202 and 204) are not directly referenced to the circuit ground 216, but are instead referenced to the circuit ground 216 via the pacing output stage circuitry.

Figure 3:
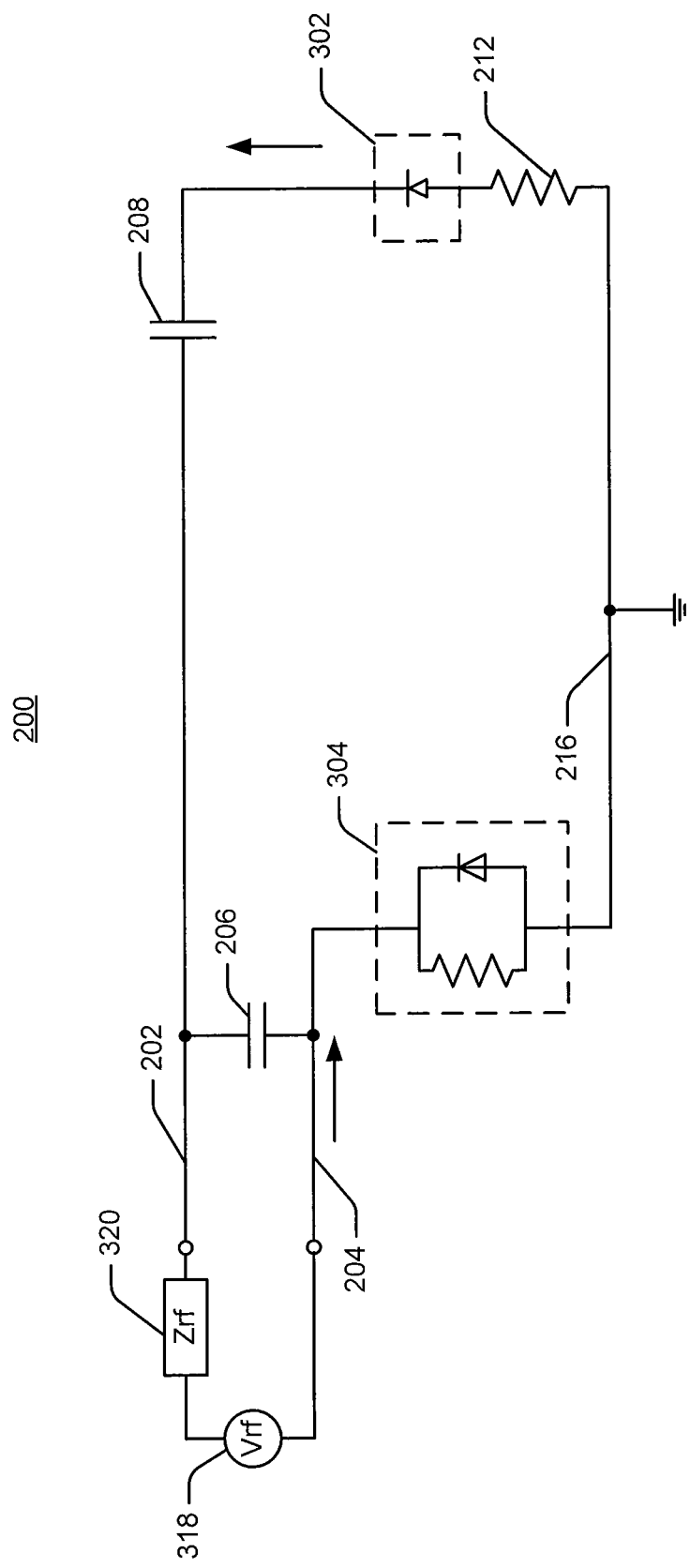
FIG. 3 is a simplified diagram illustrating sample equivalent circuits for the internal circuitry of FIG. 2.

FIG. 3 illustrates the pacing output stage of FIG. 2 during a fast recharge operation (e.g., during left ventricle fast recharge) showing equivalent circuit 302 and 304 for the return switch 210 and the fast discharge switch 214, respectively. When a pacing pulse is not being applied to a patient (e.g., during recharge), the return switch 210 is turned off (i.e., the switch is "open"). In contrast, the equivalent circuit 304 for the fast discharge switch may have an effective resistance on the order of 40 ohms.

FIG. 3 also illustrates a hypothetical signal source 318 and a hypothetical source impedance 320 that may be associated with the generation of an MRI-induced signal that is injected into the device 200 via the electrode circuits 202 and 204 (e.g., via a cardiac lead coupled to the device 200). As discussed herein, pulsed magnetic gradients used during MRI scanning may induce current in a "circuit" consisting of the lead, the device and patient tissue.

Under certain circumstances it is possible that rectification of this MRI-induced signal may occur within the pacing output circuitry (e.g., via ground-referenced transistors or diodes). For example, as shown in the equivalent circuits 302 and 304, parasitic diodes of the field effect transistors (FETs) in the pacing output stage circuitry may cause rectification of incoming RF current. Accordingly, a rectified signal may exit the device 200 as represented by the current flow arrows of FIG. 3.

Figure 4:
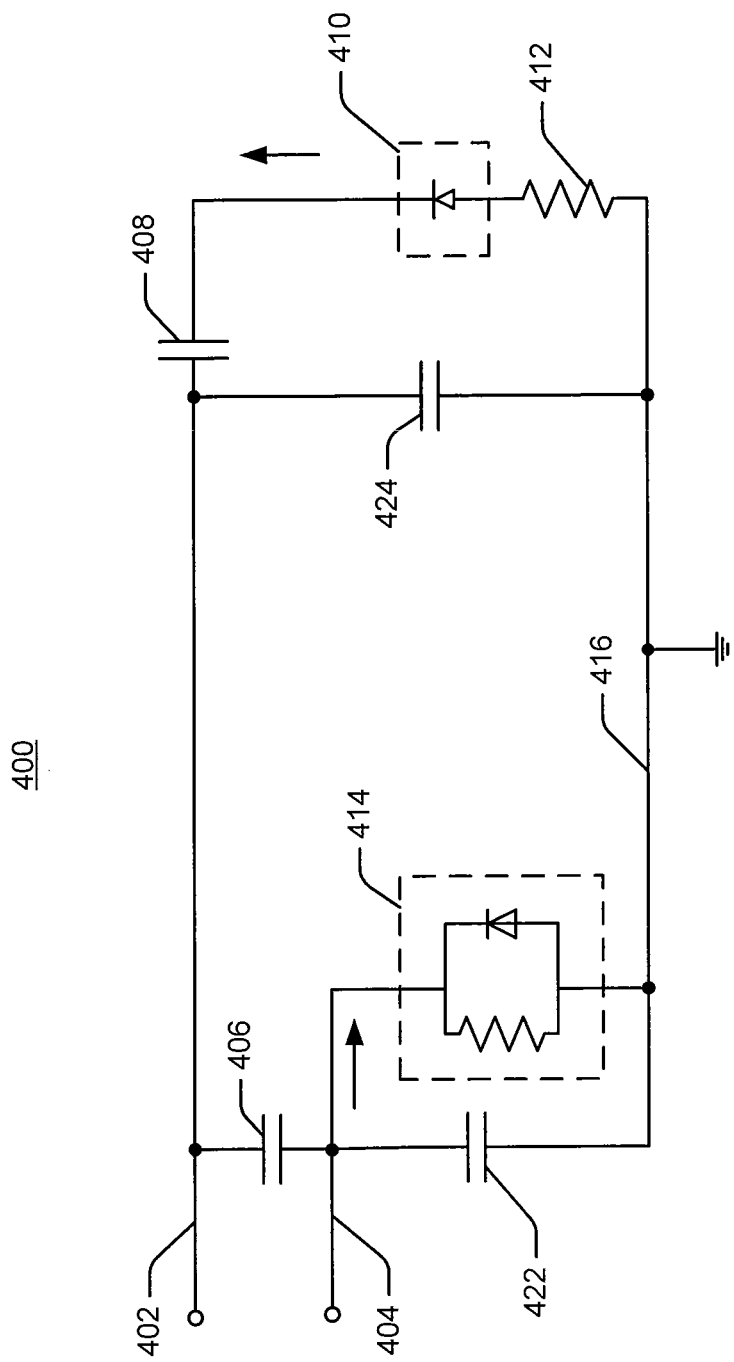
FIG. 4 is a simplified diagram of a modification of FIG. 3 that includes an embodiment of a filter circuit for filtering MRI-induced signals.

FIG. 4 depicts an embodiment of an external interface of a cardiac stimulation device 400 that illustrates how a voltage divider as taught herein may be employed in the circuit of FIG. 3. In FIG. 4, electrode circuits 402 and 404, feedthrough capacitor 406, pacing series capacitor 408, equivalent return switch circuit 410, return resistor 412, equivalent fast discharge switch circuit 414, and circuit ground 416 correspond to similar components of FIG. 3. In this case, however, the feedthrough capacitor 406 may have a lower capacitance value than the feedthrough capacitor 206 (e.g., 1.5 nanofarads instead of 4.7 nanofarads) to reduce MRI-induced current in an implantable cardiac lead (not shown in FIG. 4) that may be coupled to the device 400.

The voltage divider is implemented in FIG. 4 by placing a first capacitor 422 between the electrode circuit 404 and the circuit ground 416 and a second capacitor 424 between the electrode circuit 402 and the circuit ground 416. The capacitor 422 (e.g., corresponding to capacitor 108 in FIG. 1) is in parallel with the circuitry including the fast discharge switch. Thus, the fast discharge switch circuit (as represented by the equivalent circuit 414) may correspond to the circuit 114 of FIG. 1. The capacitor 424 (e.g., corresponding to capacitor 106 in FIG. 1) is in parallel with the circuitry including the return switch. Thus, this circuitry (as represented by the capacitor 408, the equivalent circuit 410, and the return resistor 412) may correspond to the circuit 112 of FIG. 1.

At MRI-related frequencies, the ground-referenced capacitors 422 and 424 act as a low impedance divider across the diodes illustrated in FIG. 4. For example, in some implementations the capacitors 422 and 424 may each have a capacitance value in the range of 500 picofarads to 5 nanofarads. Consequently, each capacitor may have an impedance on the order of 5 to 0.5 ohms at 64 MHz or 2.5 to 0.25 ohms at 128 MHz.

Any MRI-induced voltage across the two circuits of the fast discharge stage is decreased due to the capacitive voltage divider effect. For example, the voltage divider is configured so that approximately half of the voltage appearing across the feedthrough capacitor appears across the fast discharge switch circuitry while the rest of this voltage appears across the return switch circuitry. That is, the voltage divider may tend to hold the device ground at a voltage that is halfway between the voltage at the electrode, circuit 402 and the voltage at the electrode circuit 404. In contrast, in the absence of the voltage divider, the fast discharge switch (in its low impedance state) will try to force the full voltage appearing across the feedthrough capacitor to appear across the return switch (operating in an open state). In that case, rectification by the parasitic diode of the return switch may occur if the RF voltage across the return switch is high enough.

Advantageously, the voltage divider reduces the MRI-induced voltage that appears across the return switch, thereby reducing the likelihood that such rectification may occur. In an implementation where the capacitors 422 and 424 are each 500 picofarads, the voltage divider places 5 ohms in parallel with return switch and with the 40 ohm resistance of the fast discharge switch at a frequency of 64 MHz. If there were 5 ohms in both legs of the voltage divider, then the RF voltage would be effectively split in half at ground, and voltage across the return switch would be effectively minimized. In the example of FIG. 4, however, the 40 ohm resistance of the fast discharge switch reduces the effective impedance of that leg of the voltage divider, causing slightly more than half the RF voltage to appear across the return switch. If the fast return switch had a lower "on" resistance, then more RF voltage would appear across the return switch. Thus, the values of the capacitors making up the voltage divider may be chosen such that: 1) the impedance of the capacitors at relevant frequencies is less than the lowest impedance of the circuitry that the capacitors bypass (e.g., their impedance may be specified to be no more than 22% of the impedance of the circuitry they bypass in order to keep ground within about 10% of the half-way point); and 2) the series combination of these capacitors in parallel with the feedthrough capacitor maintains sufficient control of gradient-induced current pulse width. The first consideration would have the voltage divider capacitor values be as large as possible, while the second consideration would have the voltage divider capacitor values be as small as possible. Therefore a design trade off is involved. It should be noted also that the optional protection diodes, such as described in FIG. 1 (134 and 136) would appear in parallel with the capacitors (422 and 424) making up the voltage divider.

Figure 5A:
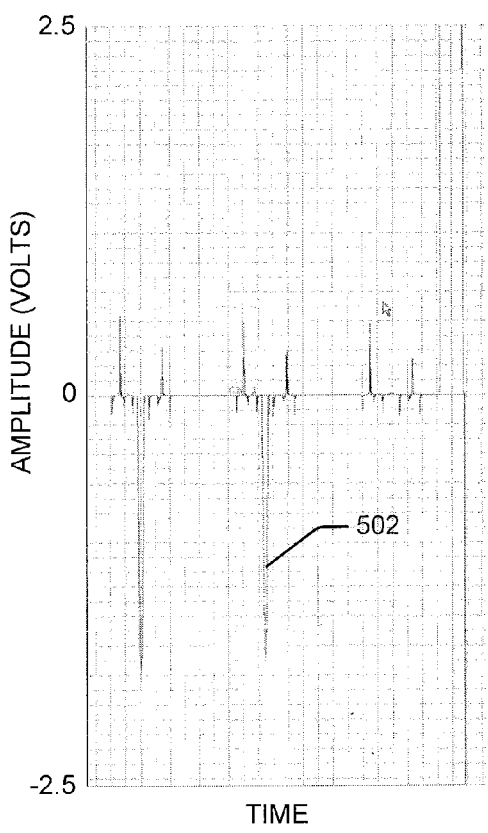
FIGS. 5A and 5B depict sample rectified signals.
Figure 5B:
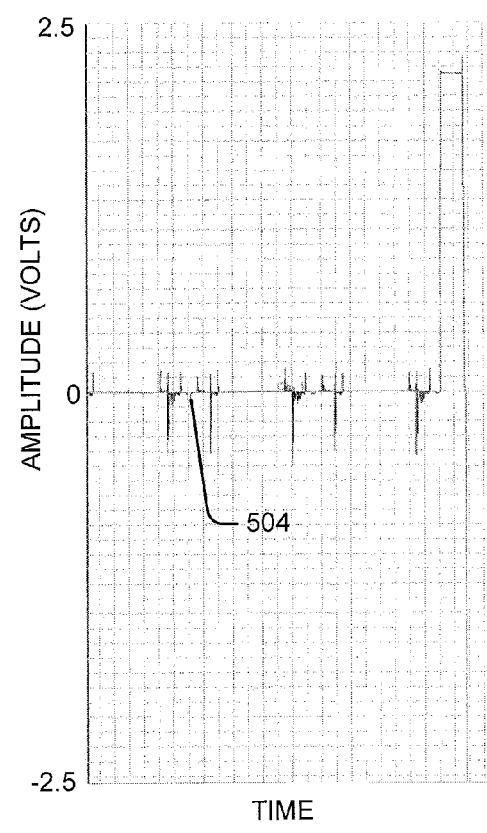

Through the use of protection circuitry as taught herein, a significant reduction in rectified RF current may be achieved. For example, FIGS. 5A and 5B illustrate sample rectified RF signals in a case where a voltage divider is not used (FIG. 5A) and in a case where 500 picofarad capacitors are provided between each electrode circuit and ground (FIG. 5B). In this example, there is nearly 1 milliamp of rectified current 502 when the voltage divider is not used, and considerably less rectified RF current 504 when the voltage divider is used (1 milliamp corresponds to approximately 2 volts in FIGS. 5A and 5B). In general, it may be desirable to configure the voltage divider circuit to limit the rectified current to a magnitude on the order of 50-200 microamps or less (e.g., as shown in FIG. 5B) to prevent potential cardiac stimulation.

Advantageously, this reduction in rectified current may be achieved without significantly increasing currents resulting from pulsed gradients during MRI. As mentioned above, the addition of voltage divider capacitors in parallel with the feedthrough capacitor may increase the effective capacitance across the input of the implantable medical device. Nevertheless, the induced gradients that occur when a voltage divider is used (e.g., with 500 picofarads capacitors) may be substantially equal to the induced gradients that occur when a voltage divider is not used (e.g., in an implementation that uses a 1.5 nanofarad feedthrough capacitor).

Figure 6:
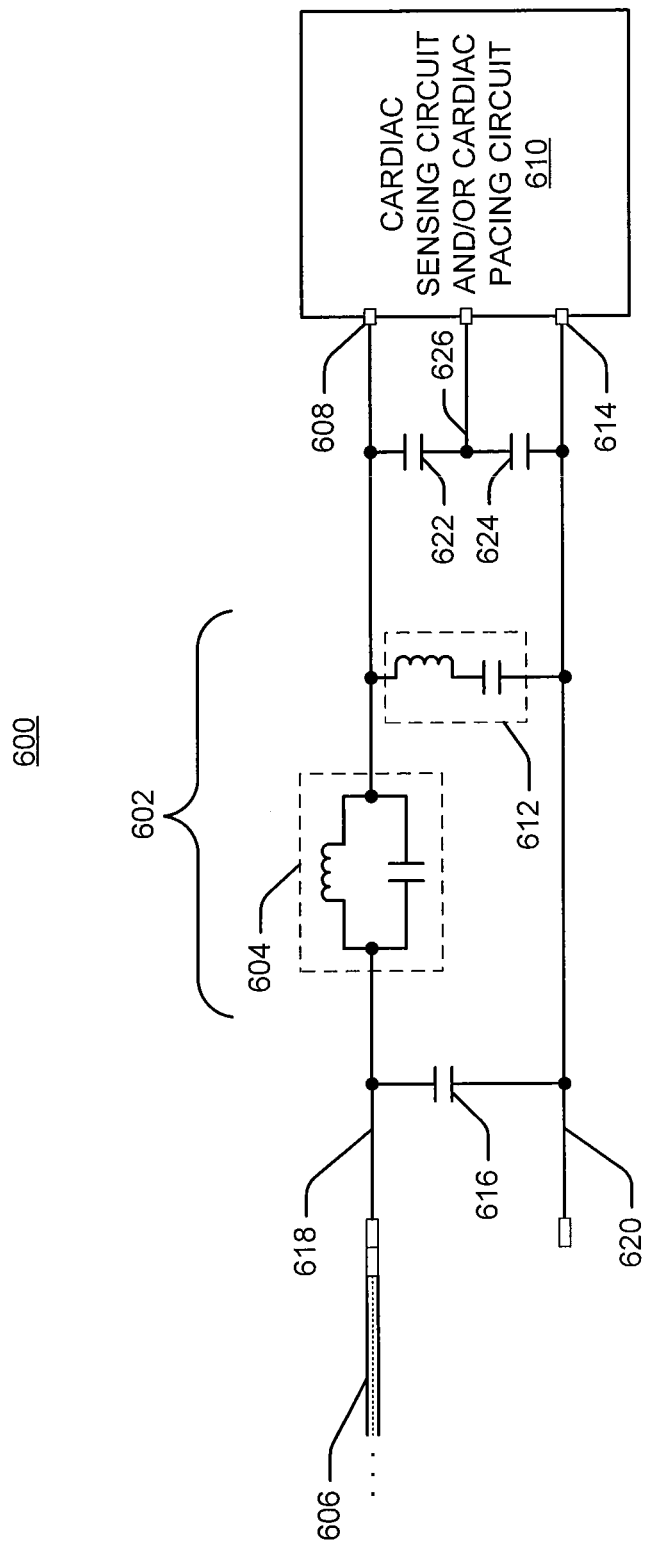
FIG. 6 is a simplified diagram illustrating a sample embodiment of a circuit for filtering MRI-induced signals.

A voltage divider as taught herein may be employed with other MRI filtering schemes. For example, FIG. 6 illustrates an implementation of an implantable medical apparatus 600 that employs resonant filter circuits 602 for reducing MRI-induced signals. In this example, an inductor-capacitor (LC) tank circuit 604 is provided in series with an implantable cardiac lead 606 coupled to a first terminal 608 of a cardiac sensing and/or pacing circuit 610, while a series LC circuit 612 is shunted across the first terminal 608 and a second terminal 614 of the circuit 610.

The LC circuits are configured to attenuate MRI-induced signals. For example, the LC tank circuit may have high impedance at MRI-related frequencies while the series LC circuit may have low impedance at MRI-related frequencies. In this way, any signals induced in the cardiac lead 606 by MRI scanning may be significantly attenuated before they enter the circuit 610.

To this end, the resonant filter circuits may be tuned to a frequency associated with MRI scanning (e.g., in the 64 MHz range, the 128 MHz range, some other frequency range, or a combination of these ranges). For example, both circuits 604 and 612 may have a resonant frequency of 64 MHz or 128 MHz. Alternatively, one of these circuits may have a resonant frequency of 64 MHz, while the other circuit has a resonant frequency of 128 MHz.

A feedthrough capacitor 616 is provided across electrode circuits 618 and 620. In some implementations, the feedthrough capacitor 616 may have a relatively low capacitance value for reducing MRI gradient currents as discussed above. In such a case, the LC tank circuit 604 and the series LC circuit 612 may serve to attenuate MRI-induced RF energy and to compensate for any potential degradation in EMI protection that may be caused by the use of a low nominal capacitance value for the feedthrough capacitor 616.

Voltage divider capacitors 622 and 624 are provided across the first and second terminals 608 and 614 of the circuit 610. As discussed herein, a center tap of the voltage divider is coupled to a ground circuit 626 of the circuit 610 to prevent rectification of MRI-induced signals. The voltage divider may thus be used in conjunction with the resonant filter circuits to further reduce the magnitude of the MRI-induced signals that enter the circuit 610.

Other resonant circuit configurations may be employed in other embodiments. For example, multiple LC tank circuits may be used instead of a single LC tank circuit and/or multiple series LC circuits may be used instead of a single series LC circuit. Also, multiple sets of LC tank and series LC circuits may be employed instead the single set shown in FIG. 6. For example, another set of LC tank and series LC circuits may be employed between the series LC circuit 612 and the voltage divider capacitors 622 and 624. In addition, input protection diodes may be employed in the example of FIG. 6 to provide additional reduction of RF voltage across internal circuitry. As described above, each leg of the capacitive voltage divider may be placed in parallel with a fast-switching diode. For example, a diode (e.g., corresponding to the diode 134 of FIG. 1) may be employed across the first terminal 608 and the ground circuit 626, and a diode (e.g., corresponding to the diode 136 of FIG. 1) may be employed across the second terminal 614 and the ground circuit 626.

Figure 7:
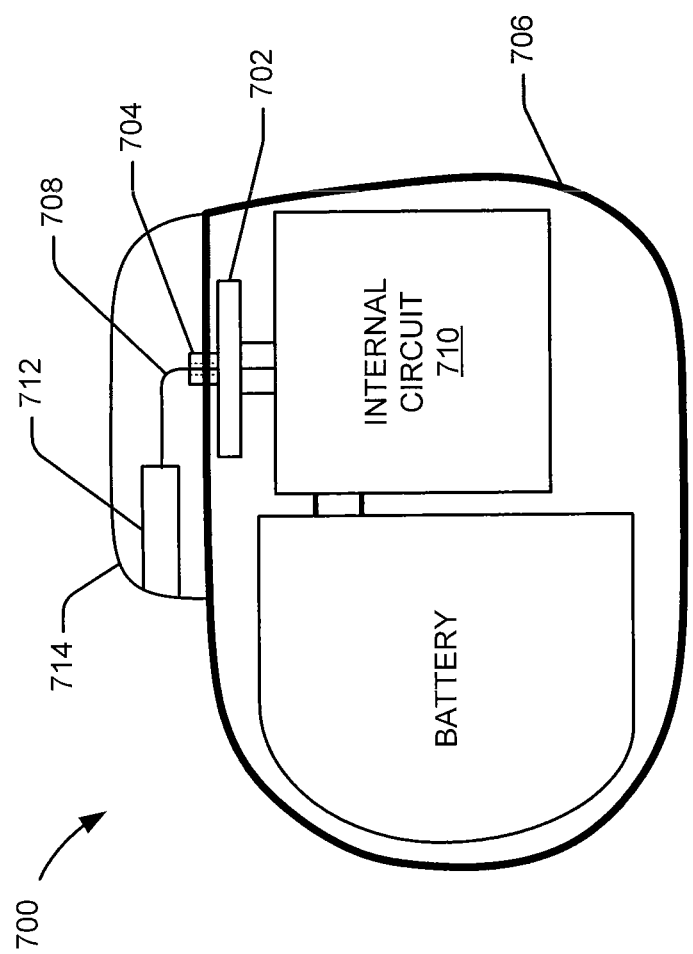
FIG. 7 is a simplified diagram of an embodiment of an implantable medical device that includes a substrate for one or more filter circuits.

FIG. 7 illustrates a sample implantable medical device 700 where at least a portion of the filter circuitry as taught herein is implemented on a substrate (e.g., on a printed circuit board) 702 placed immediately after a feedthrough 704 of the implantable medical device 700. Here, the feedthrough 704 is hermetically sealed to a conductive, biocompatible housing 706 of the device 700, and also provides a hermetically sealed passage for one or more conductors 708 that enable signals be coupled between an internal circuit 710 and an external connector 712 (provided within a header 714) of the device 700. The substrate 702 may be mounted onto the feedthrough 704 so that the filter circuits are as close as possible to the feedthrough to reduce the amount of stray RF energy that may be radiated via the conductor(s) 708 inside the housing 706.

Various components may be provided on the substrate 702. For example, in some implementations at least a portion of the feedthrough capacitance may be implemented on the substrate 702 (e.g., instead of within the feedthrough 704). In some implementations one or more filter circuits (e.g., one or more of filter circuits 106, 108, 422, 424, 604, 612, 622, or 624) may be implemented on the substrate 702.

In practice, filter circuitry for multiple channels (for multiple cardiac leads) may be implemented on the substrate 702. Given the excellent current and voltage attenuation that may be achieved by this filter circuitry, crosstalk interference may be negligible even when a relatively small substrate having minimal PCB trace clearance is employed. It should be noted that any inductors employed in this design may have non-magnetic cores. Magnetic cores would be likely to saturate in the strong MRI static field, drastically altering inductance values.

Figure 8:
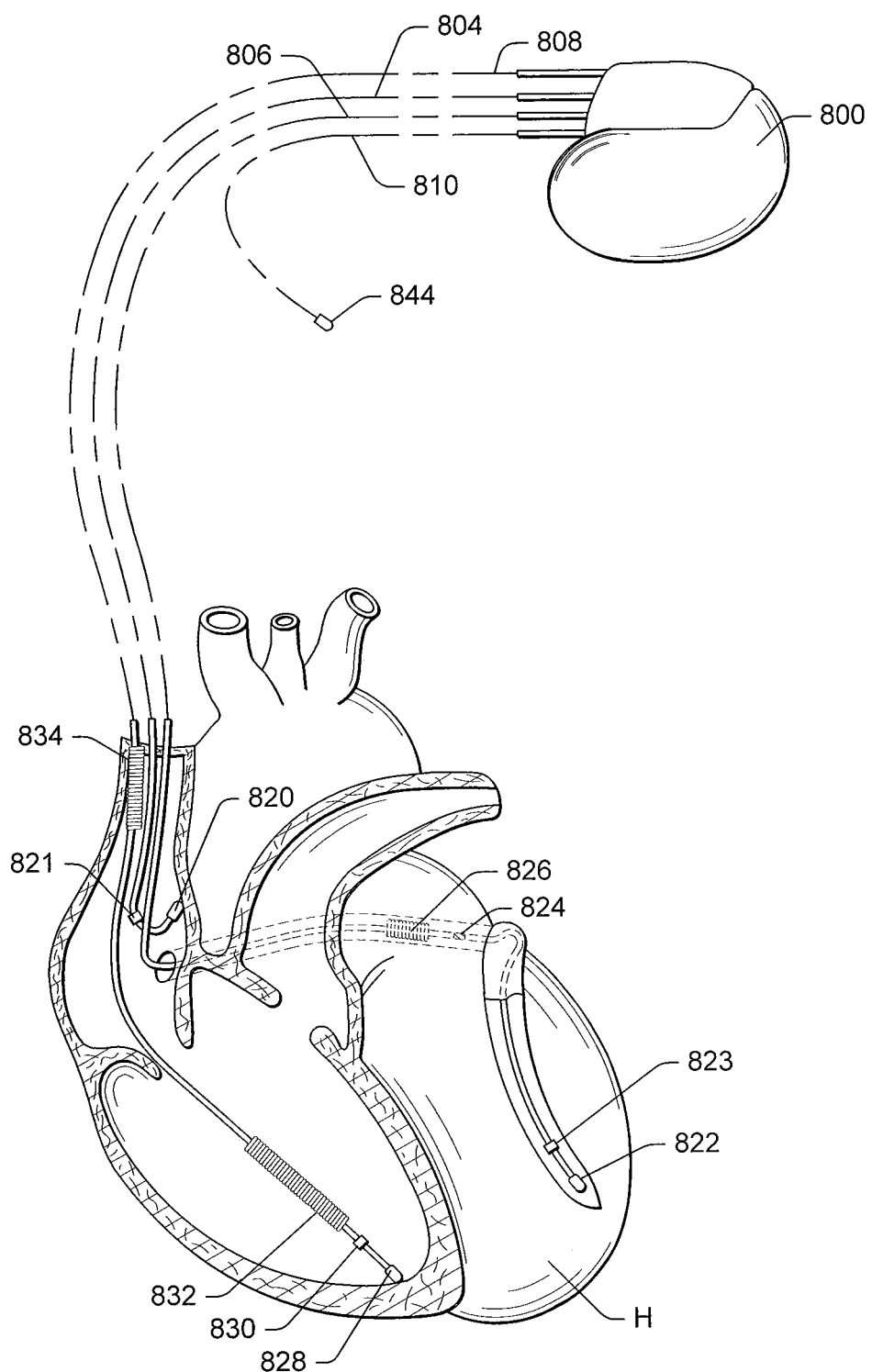
FIG. 8 is a simplified diagram of an embodiment of an implantable cardiac device in electrical communication with one or more leads implanted in a patient's heart for sensing conditions in the patient, delivering therapy to the patient, or providing some combination thereof.
Figure 9:
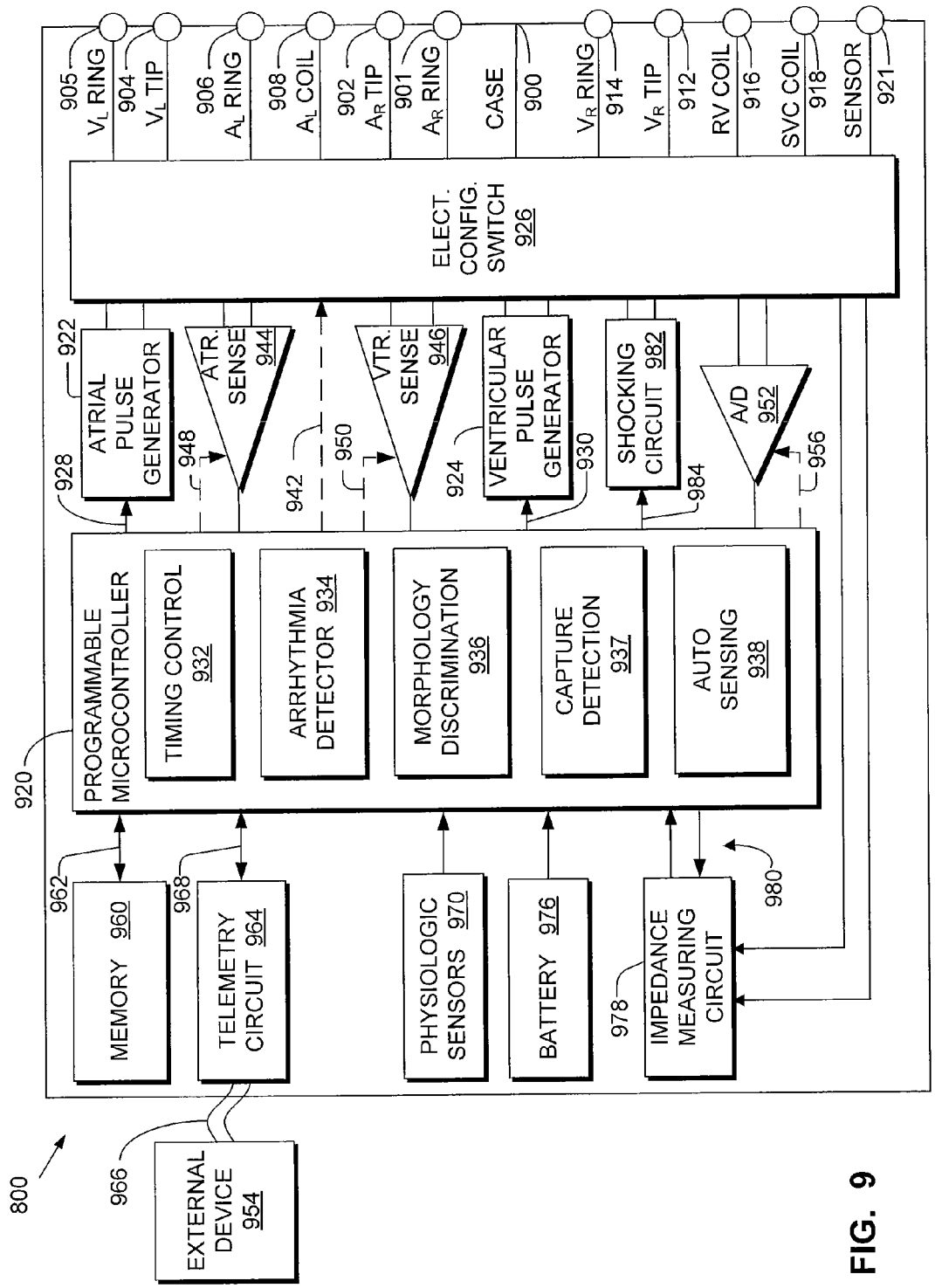
FIG. 9 is a simplified functional block diagram of an embodiment of an implantable cardiac device, illustrating basic elements that may be configured to sense conditions in the patient, deliver therapy to the patient, or provide some combination thereof.

FIGS. 8 and 9 describe an exemplary implantable medical device (e.g., a stimulation device such as a pacemaker, an implantable cardioverter defibrillator, etc.) that is capable of being used in connection with the various embodiments that are described herein. It is to be appreciated and understood that other devices, including those that are not necessarily implantable, can be used and that the description below is given, in its specific context, to assist the reader in understanding, with more clarity, the embodiments described herein.

FIG. 8 shows an exemplary implantable cardiac device 800 in electrical communication with a patient's heart H by way of three leads 804, 806, and 808, suitable for delivering multi-chamber stimulation and shock therapy. Bodies of the leads 804, 806, and 808 may be formed of silicone, polyurethane, plastic, or similar biocompatible materials to facilitate implant within a patient. Each lead includes one or more conductors, each of which may couple one or more electrodes incorporated into the lead to a connector on the proximal end of the lead. Each connector, in turn, is configured to couple with a complimentary connector (e.g., implemented within a header) of the device 800.

To sense atrial cardiac signals and to provide right atrial chamber stimulation therapy, the device 800 is coupled to an implantable right atrial lead 804 having, for example, an atrial tip electrode 820, which typically is implanted in the patient's right atrial appendage or septum. FIG. 8 also shows the right atrial lead 804 as having an optional atrial ring electrode 821.

To sense left atrial and ventricular cardiac signals and to provide left chamber pacing therapy, the device 800 is coupled to a coronary sinus lead 806 designed for placement in the coronary sinus region via the coronary sinus for positioning one or more electrodes adjacent to the left ventricle, one or more electrodes adjacent to the left atrium, or both. As used herein, the phrase "coronary sinus region" refers to the vasculature of the left ventricle, including any portion of the coronary sinus, the great cardiac vein, the left marginal vein, the left posterior ventricular vein, the middle cardiac vein, the small cardiac vein or any other cardiac vein accessible by the coronary sinus.

Accordingly, an exemplary coronary sinus lead 806 is designed to receive atrial and ventricular cardiac signals and to deliver left ventricular pacing therapy using, for example, a left ventricular tip electrode 822 and, optionally, a left ventricular ring electrode 823; provide left atrial pacing therapy using, for example, a left atrial ring electrode 824; and provide shocking therapy using, for example, a left atrial coil electrode 826 (or other electrode capable of delivering a shock). For a more detailed description of a coronary sinus lead, the reader is directed to U.S. Pat. No. 5,466,254, "Coronary Sinus Lead with Atrial Sensing Capability" (Helland), which is incorporated herein by reference.

The device 800 is also shown in electrical communication with the patient's heart H by way of an implantable right ventricular lead 808 having, in this implementation, a right ventricular tip electrode 828, a right ventricular ring electrode 830, a right ventricular (RV) coil electrode 832 (or other electrode capable of delivering a shock), and a superior vena cava (SVC) coil electrode 834 (or other electrode capable of delivering a shock). Typically, the right ventricular lead 808 is transvenously inserted into the heart H to place the right ventricular tip electrode 828 in the right ventricular apex so that the RV coil electrode 832 will be positioned in the right ventricle and the SVC coil electrode 834 will be positioned in the superior vena cava. Accordingly, the right ventricular lead 808 is capable of sensing or receiving cardiac signals, and delivering stimulation in the form of pacing and shock therapy to the right ventricle.

The device 800 is also shown in electrical communication with a lead 810 including one or more components 844 such as a physiologic sensor. The component 844 may be positioned in, near or remote from the heart.

It should be appreciated that the device 800 may connect to leads other than those specifically shown. In addition, the leads connected to the device 800 may include components other than those specifically shown. For example, a lead may include other types of electrodes, sensors or devices that serve to otherwise interact with a patient or the surroundings.

FIG. 9 depicts an exemplary, simplified block diagram illustrating sample components of the device 800. The device 800 may be adapted to treat both fast and slow arrhythmias with stimulation therapy, including cardioversion, defibrillation, and pacing stimulation. While a particular multi-chamber device is shown, it is to be appreciated and understood that this is done for illustration purposes. Thus, the techniques and methods described below can be implemented in connection with any suitably configured or configurable device. Accordingly, one of skill in the art could readily duplicate, eliminate, or disable the appropriate circuitry in any desired combination to provide a device capable of treating the appropriate chamber(s) with, for example, cardioversion, defibrillation, and pacing stimulation.

A housing 900 for the device 800 is often referred to as the "can", "case" or "case electrode", and may be programmably selected to act as the return electrode for all "unipolar" modes. The housing 900 may further be used as a return electrode alone or in combination with one or more of the coil electrodes 826, 832 and 834 for shocking purposes. The housing 900 may be constructed of a biocompatible material (e.g., titanium) to facilitate implant within a patient.

The housing 900 further includes a connector (not shown) having a plurality of terminals 901, 902, 904, 905, 906, 908, 912, 914, 916 and 918 (shown schematically and, for convenience, the names of the electrodes to which they are connected are shown next to the terminals). The connector may be configured to include various other terminals (e.g., terminal 921 coupled to a sensor or some other component) depending on the requirements of a given application.

To achieve right atrial sensing and pacing, the connector includes, for example, a right atrial tip terminal (AR TIP) 902 adapted for connection to the right atrial tip electrode 820. A right atrial ring terminal (AR RING) 901 may also be included and adapted for connection to the right atrial ring electrode 821. To achieve left chamber sensing, pacing, and shocking, the connector includes, for example, a left ventricular tip terminal (VL TIP) 904, a left ventricular ring terminal (VL RING) 905, a left atrial ring terminal (AL RING) 906, and a left atrial shocking terminal (AL COIL) 908, which are adapted for connection to the left ventricular tip electrode 822, the left ventricular ring electrode 823, the left atrial ring electrode 824, and the left atrial coil electrode 826, respectively.

To support right chamber sensing, pacing, and shocking, the connector further includes a right ventricular tip terminal (VR TIP) 912, a right ventricular ring terminal (VR RING) 914, a right ventricular shocking terminal (RV COIL) 916, and a superior vena cava shocking terminal (SVC COIL) 918, which are adapted for connection to the right ventricular tip electrode 828, the right ventricular ring electrode 830, the RV coil electrode 832, and the SVC coil electrode 834, respectively.

At the core of the device 800 is a programmable microcontroller 920 that controls the various modes of stimulation therapy. As is well known in the art, microcontroller 920 typically includes a microprocessor, or equivalent control circuitry, designed specifically for controlling the delivery of stimulation therapy, and may further include memory such as RAM, ROM and flash memory, logic and timing circuitry, state machine circuitry, and I/O circuitry. Typically, microcontroller 920 includes the ability to process or monitor input signals (data or information) as controlled by a program code stored in a designated block of memory. The type of microcontroller is not critical to the described implementations. Rather, any suitable microcontroller 920 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals that may be used within the device and their inter-relationship, see U.S. Pat. No. 4,788,980 (Mann et al.), also incorporated herein by reference.

FIG. 9 also shows an atrial pulse generator 922 and a ventricular pulse generator 924 that generate pacing stimulation pulses for delivery by the right atrial lead 804, the coronary sinus lead 806, the right ventricular lead 808, or some combination of these leads via an electrode configuration switch 926. It is understood that in order to provide stimulation therapy in each of the four chambers of the heart, the atrial and ventricular pulse generators 922 and 924 may include dedicated, independent pulse generators, multiplexed pulse generators, or shared pulse generators. The pulse generators 922 and 924 are controlled by the microcontroller 920 via appropriate control signals 928 and 930, respectively, to trigger or inhibit the stimulation pulses.

Microcontroller 920 further includes timing control circuitry 932 to control the timing of the stimulation pulses (e.g., pacing rate, atrio-ventricular (A-V) delay, atrial interconduction (A-A) delay, or ventricular interconduction (V-V) delay, etc.) or other operations, as well as to keep track of the timing of refractory periods, blanking intervals, noise detection windows, evoked response windows, alert intervals, marker channel timing, etc., as known in the art.

Microcontroller 920 further includes an arrhythmia detector 934. The arrhythmia detector 934 may be utilized by the device 800 for determining desirable times to administer various therapies. The arrhythmia detector 934 may be implemented, for example, in hardware as part of the microcontroller 920, or as software/firmware instructions programmed into the device 800 and executed on the microcontroller 920 during certain modes of operation.

Microcontroller 920 may include a morphology discrimination module 936, a capture detection module 937 and an auto sensing module 938. These modules are optionally used to implement various exemplary recognition algorithms or methods. The aforementioned components may be implemented, for example, in hardware as part of the microcontroller 920, or as software/firmware instructions programmed into the device 800 and executed on the microcontroller 920 during certain modes of operation.

The electrode configuration switch 926 includes a plurality of switches for connecting the desired terminals (e.g., that are connected to electrodes, coils, sensors, etc.) to the appropriate I/O circuits, thereby providing complete terminal and, hence, electrode programmability. Accordingly, switch 926, in response to a control signal 942 from the microcontroller 920, may be used to determine the polarity of the stimulation pulses (e.g., unipolar, bipolar, combipolar, etc.) by selectively closing the appropriate combination of switches (not shown) as is known in the art.

Atrial sensing circuits (ATR. SENSE) 944 and ventricular sensing circuits (VTR. SENSE) 946 may also be selectively coupled to the right atrial lead 804, coronary sinus lead 806, and the right ventricular lead 808, through the switch 926 for detecting the presence of cardiac activity in each of the four chambers of the heart. Accordingly, the atrial and ventricular sensing circuits 944 and 946 may include dedicated sense amplifiers, multiplexed amplifiers, or shared amplifiers. Switch 926 determines the "sensing polarity" of the cardiac signal by selectively closing the appropriate switches, as is also known in the art. In this way, the clinician may program the sensing polarity independent of the stimulation polarity. The sensing circuits (e.g., circuits 944 and 946) are optionally capable of obtaining information indicative of tissue capture.

Each sensing circuit 944 and 946 preferably employs one or more low power, precision amplifiers with programmable gain, automatic gain control, bandpass filtering, a threshold detection circuit, or some combination of these components, to selectively sense the cardiac signal of interest. The automatic gain control enables the device 800 to deal effectively with the difficult problem of sensing the low amplitude signal characteristics of atrial or ventricular fibrillation.

The outputs of the atrial and ventricular sensing circuits 944 and 946 are connected to the microcontroller 920, which, in turn, is able to trigger or inhibit the atrial and ventricular pulse generators 922 and 924, respectively, in a demand fashion in response to the absence or presence of cardiac activity in the appropriate chambers of the heart. Furthermore, as described herein, the microcontroller 920 is also capable of analyzing information output from the sensing circuits 944 and 946, a data acquisition system 952, or both. This information may be used to determine or detect whether and to what degree tissue capture has occurred and to program a pulse, or pulses, in response to such determinations. The sensing circuits 944 and 946, in turn, receive control signals over signal lines 948 and 950, respectively, from the microcontroller 920 for purposes of controlling the gain, threshold, polarization charge removal circuitry (not shown), and the timing of any blocking circuitry (not shown) coupled to the inputs of the sensing circuits 944 and 946 as is known in the art.

For arrhythmia detection, the device 800 utilizes the atrial and ventricular sensing circuits 944 and 946 to sense cardiac signals to determine whether a rhythm is physiologic or pathologic. It should be appreciated that other components may be used to detect arrhythmia depending on the system objectives. In reference to arrhythmias, as used herein, "sensing" is reserved for the noting of an electrical signal or obtaining data (information), and "detection" is the processing (analysis) of these sensed signals and noting the presence of an arrhythmia.

Timing intervals between sensed events (e.g., P-waves, R-waves, and depolarization signals associated with fibrillation) may be classified by the arrhythmia detector 934 of the microcontroller 920 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules may be applied to the atrial channel to determine if there is an atrial tachyarrhythmia or atrial fibrillation with appropriate classification and intervention.

Cardiac signals or other signals may be applied to inputs of an analog-to-digital (A/D) data acquisition system 952. The data acquisition system 952 is configured (e.g., via signal line 956) to acquire intracardiac electrogram ("IEGM") signals or other signals, convert the raw analog data into a digital signal, and store the digital signals for later processing, for telemetric transmission to an external device 954, or both. For example, the data acquisition system 952 may be coupled to the right atrial lead 804, the coronary sinus lead 806, the right ventricular lead 808 and other leads through the switch 926 to sample cardiac signals across any pair of desired electrodes.

The data acquisition system 952 also may be coupled to receive signals from other input devices. For example, the data acquisition system 952 may sample signals from a physiologic sensor 970 or other components shown in FIG. 9 (connections not shown).

The microcontroller 920 is further coupled to a memory 960 by a suitable data/address bus 962, wherein the programmable operating parameters used by the microcontroller 920 are stored and modified, as required, in order to customize the operation of the device 800 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart H within each respective tier of therapy. One feature of the described embodiments is the ability to sense and store a relatively large amount of data (e.g., from the data acquisition system 952), which data may then be used for subsequent analysis to guide the programming of the device 800.

Advantageously, the operating parameters of the implantable device 800 may be non-invasively programmed into the memory 960 through a telemetry circuit 964 in telemetric communication via communication link 966 with the external device 954, such as a programmer, transtelephonic transceiver, a diagnostic system analyzer or some other device. The microcontroller 920 activates the telemetry circuit 964 with a control signal (e.g., via bus 968). The telemetry circuit 964 advantageously allows intracardiac electrograms and status information relating to the operation of the device 800 (as contained in the microcontroller 920 or memory 960) to be sent to the external device 954 through an established communication link 966.

The device 800 can further include one or more physiologic sensors 970. In some embodiments the device 800 may include a "rate-responsive" sensor that may provide, for example, information to aid in adjustment of pacing stimulation rate according to the exercise state of the patient. One or more physiologic sensors 970 (e.g., a pressure sensor) may further be used to detect changes in cardiac output, changes in the physiological condition of the heart, or diurnal changes in activity (e.g., detecting sleep and wake states). Accordingly, the microcontroller 920 responds by adjusting the various pacing parameters (such as rate, A-V Delay, V-V Delay, etc.) at which the atrial and ventricular pulse generators 922 and 924 generate stimulation pulses.

While shown as being included within the device 800, it is to be understood that a physiologic sensor 970 may also be external to the device 800, yet still be implanted within or carried by the patient. Examples of physiologic sensors that may be implemented in conjunction with the device 800 include sensors that sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), which patent is hereby incorporated by reference.

The one or more physiologic sensors 970 may optionally include one or more of components to help detect movement (via, e.g., a position sensor or an accelerometer) and minute ventilation (via an MV sensor) in the patient. Signals generated by the position sensor and MV sensor may be passed to the microcontroller 920 for analysis in determining whether to adjust the pacing rate, etc. The microcontroller 920 may thus monitor the signals for indications of the patient's position and activity status, such as whether the patient is climbing up stairs or descending down stairs or whether the patient is sitting up after lying down.

The device 800 additionally includes a battery 976 that provides operating power to all of the circuits shown in FIG. 9. For a device 800 which employs shocking therapy, the battery 976 is capable of operating at low current drains (e.g., preferably less than 10 μA) for long periods of time, and is capable of providing high-current pulses (for capacitor charging) when the patient requires a shock pulse (e.g., preferably, in excess of 2 A, at voltages above 200 V, for periods of 10 seconds or more). The battery 976 also desirably has a predictable discharge characteristic so that elective replacement time can be detected. Accordingly, the device 800 preferably employs lithium or other suitable battery technology.

The device 800 can further include magnet detection circuitry (not shown), coupled to the microcontroller 920, to detect when a magnet is placed over the device 800. A magnet may be used by a clinician to perform various test functions of the device 800 and to signal the microcontroller 920 that the external device 954 is in place to receive data from or transmit data to the microcontroller 920 through the telemetry circuit 964.

The device 800 further includes an impedance measuring circuit 978 that is enabled by the microcontroller 920 via a control signal 980. The known uses for an impedance measuring circuit 978 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device 800 has been implanted; measuring stroke volume; and detecting the opening of heart valves, etc. The impedance measuring circuit 978 is advantageously coupled to the switch 926 so that any desired electrode may be used.

In the case where the device 800 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 920 further controls a shocking circuit 982 by way of a control signal 984. The shocking circuit 982 generates shocking pulses of low (e.g., up to 0.5 J), moderate (e.g., 0.5 J to 10 J), or high energy (e.g., 11 J to 40 J), as controlled by the microcontroller 920. Such shocking pulses are applied to the patient's heart H through, for example, two shocking electrodes and as shown in this embodiment, selected from the left atrial coil electrode 826, the RV coil electrode 832 and the SVC coil electrode 834. As noted above, the housing 900 may act as an active electrode in combination with the RV coil electrode 832, as part of a split electrical vector using the SVC coil electrode 834 or the left atrial coil electrode 826 (i.e., using the RV electrode as a common electrode), or in some other arrangement.

Cardioversion level shocks are generally considered to be of low to moderate energy level (so as to minimize pain felt by the patient), be synchronized with an R-wave, pertain to the treatment of tachycardia, or some combination of the above. Defibrillation shocks are generally of moderate to high energy level (i.e., corresponding to thresholds in the range of 5 J to 40 J), delivered asynchronously (since R-waves may be too disorganized), and pertaining to the treatment of fibrillation. Accordingly, the microcontroller 920 is capable of controlling the synchronous or asynchronous delivery of the shocking pulses.

The filter circuits described herein may be implemented at or near one or more of the components of FIG. 9. For example, a feedthrough capacitor and/or a voltage divider circuit may be implanted at or near the connector, the switch 926, the sense circuits 944 and 946, or the pulse generator circuits 922 and 924.

Various modifications may be incorporated into the disclosed embodiments based on the teachings herein. For example, the structure and functionality taught herein may be incorporated into types of devices other than the specific types of devices described above. In addition, different filtering components and filtering schemes may be employed consistent with the teachings herein.

The various structures and functions described herein may be incorporated into a variety of apparatuses (e.g., a stimulation device, a lead, a monitoring device, etc.) and implemented in a variety of ways. Different embodiments of such an apparatus may include a variety of hardware and software processing components. In some embodiments, hardware components such as processors, controllers, state machines, logic, or some combination of these components, may be used to implement the described components or circuits.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

Moreover, some of the operations described herein may be performed by a device that is located externally with respect to the body of the patient. For example, an implanted device may send raw data or processed data to an external device that then performs the necessary processing.

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, on a circuit board or implemented as discrete wires or in other ways.

As used herein, terminology describing the coupling of components refers to any mechanism that allows signals to travel from one component to another. Thus, coupling may be accomplished through use of an electrical conductor and/or an electrical component (e.g., an active or passive electrical circuit). In some cases two or more components may be "directly coupled." That is, the components may be coupled via a conductor without any intervening components (e.g., an active or passive electrical circuit) between the components. Also, the term circuit is used herein in a broad sense of a component or components through which current may flow, and is not limited to the narrower definition of a structure that forms a loop. For example, a circuit may comprise one component (e.g., a conductor, an electronic component, etc.) or more than one component (e.g., several electronic components connected by one or more conductors). As a specific example, a ground circuit may take the form of a single conductor, a ground plane, multiple conductors, multiple ground planes, or some other form. As another specific example, an electrode circuit may take the form of a single conductor, a conductor and a connector, multiple conductors, or some other form.

The signals discussed herein may take various forms. For example, in some embodiments a signal may comprise electrical signals transmitted over a wire, light pulses transmitted through an optical medium such as an optical fiber or air, or RF waves transmitted through a medium such as air, and so on. In addition, a plurality of signals may be collectively referred to as a signal herein. The signals discussed above also may take the form of data. For example, in some embodiments an application program may send a signal to another application program. Such a signal may be stored in a data memory.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

Also, it should be understood that any reference to elements herein using a designation such as "first," "second," and so forth does not generally limit the quantity or order of those elements. Rather, these designations may be used herein as a convenient method of distinguishing between two or more different elements or instances of an element. Thus, a reference to first and second elements does not mean that only two elements may be employed there or that the first element must precede the second element in some manner. Also, unless stated otherwise a set of elements may comprise one or more elements.

While certain embodiments have been described above in detail and shown in the accompanying drawings, it is to be understood that such embodiments are merely illustrative of and not restrictive of the teachings herein. In particular, it should be recognized that the teachings herein apply to a wide variety of apparatuses and methods. It will thus be recognized that various modifications may be made to the illustrated embodiments or other embodiments, without departing from the broad scope thereof. In view of the above it will be understood that the teachings herein are intended to cover any changes, adaptations or modifications which are within the scope of the disclosure.

What is claimed is:

1. An implantable medical apparatus, comprising:
   a first electrode circuit;
   a second electrode circuit;
   a feedthrough capacitor coupled between the first electrode circuit and the second electrode circuit;
   a cardiac signal processing circuit comprising a first terminal, a second terminal, and a ground circuit, wherein the second terminal is coupled to the second cardiac electrode circuit;
   an LC tank circuit coupled between the first electrode circuit and the first terminal of the cardiac signal processing circuit;
   a series LC circuit coupled between the second electrode circuit and the first terminal of the cardiac signal processing circuit; and
   a voltage divider circuit coupled between the first terminal of the cardiac signal processing circuit and the second terminal of the cardiac signal processing circuit, wherein a center tap of the voltage divider circuit is coupled to the ground circuit.

2. The implantable medical apparatus of claim 1, further comprising:
   a first diode coupled between the first electrode circuit and the ground circuit; and
   a second diode coupled between the second electrode circuit and the ground circuit.

3. The implantable medical apparatus of claim 1, wherein:
   the voltage divider circuit comprises a first capacitor and a second capacitor;
   the first capacitor is coupled between the first terminal of the cardiac signal processing circuit and the ground circuit; and
   the second capacitor is coupled between the second terminal of the cardiac signal processing circuit and the ground circuit.

4. The implantable medical apparatus of claim 3, wherein the cardiac signal processing circuit comprises:
   a first cardiac pacing circuit coupled between the first terminal of the cardiac signal processing circuit and the ground circuit; and
   a second cardiac pacing circuit coupled between the second terminal of the cardiac signal processing circuit and the ground circuit.

5. The implantable medical apparatus of claim 4, wherein the cardiac signal processing circuit further comprises a cardiac sensing circuit.

6. The implantable medical apparatus of claim 3, wherein the feedthrough capacitor has a capacitance of less than two nanofarads.

* * * * *